United States Patent [19]

Betzing et al.

[11] Patent Number: 5,776,492
[45] Date of Patent: Jul. 7, 1998

[54] RAPIDLY DISINTEGRATING MEDICINAL FORM OF TRAMADOL OR A TRAMADOL SALT

[75] Inventors: Juergen Betzing; Johannes Heinrich Antonious Bartholomaeus, both of Aachen, Germany

[73] Assignee: Gruenenthal GmbH, Aachen, Germany

[21] Appl. No.: 699,623

[22] Filed: Aug. 19, 1996

[30] Foreign Application Priority Data

Aug. 19, 1995 [DE] Germany ............ 195 30 575.2

[51] Int. Cl.$^6$ ............................................. A61K 9/20
[52] U.S. Cl. ............................................. 424/465; 424/464
[58] Field of Search ............................. 424/464, 465, 424/466

[56] References Cited

U.S. PATENT DOCUMENTS

| | | | |
|---|---|---|---|
| 3,181,998 | 5/1965 | Kanig | 167/82 |
| 4,832,956 | 5/1989 | Gergely et al. | 424/466 |
| 5,211,957 | 5/1993 | Hagemann et al. | 424/466 |
| 5,254,355 | 10/1993 | Smith et al. | 426/548 |

FOREIGN PATENT DOCUMENTS

| | | |
|---|---|---|
| 124027 | 11/1984 | European Pat. Off. . |
| 130683 | 1/1985 | European Pat. Off. . |
| 1617343 | 4/1976 | Germany . |
| 3909520 | 10/1989 | Germany . |
| WO 87/01936 | 4/1987 | WIPO . |

*Primary Examiner*—James M. Spear
*Attorney, Agent, or Firm*—Evenson, McKeown, Edwards & Lenahan P.L.L.C.

[57] ABSTRACT

Rapidly disintegrating, binder-free tablets of tramadol or a tramadol salt for oral administration comprising microcrystalline cellulose and tramadol or a pharmaceutically acceptable tramadol salt in a weight ratio of at least 2:1.

6 Claims, No Drawings

RAPIDLY DISINTEGRATING MEDICINAL FORM OF TRAMADOL OR A TRAMADOL SALT

BACKGROUND OF THE INVENTION

This invention relates to binder-free tablets of tramadol or of a tramadol salt for oral application.

In order to obtain the fastest possible, defined release of active ingredient for solid forms of medication such as tablets, a very rapid disintegration of the form of medication must be achieved in the release medium. Disintegration, namely the falling apart of the tablets into individual particles of granular material, is influenced by numerous factors: thus binders (granulating agents), lubricants and fillers, and the solubility of fillers in particular, can considerably reduce the rate of disintegration. Moreover, the size and shape of the particles, as well as the hardness of the tablets, which depends on the pressing force employed in their manufacture, have a strong influence on the rate of disintegration. In many cases, the time of disintegration increases significantly above a given tablet hardness.

The rate of disintegration of tablets can be increased by the use of disintegrating agents. Disintegrating agents are substances which are capable of accelerating the disintegration of tablets in contact with water, buffer solutions or digestive juices. Examples of known disintegrating agents include starch, sodium carboxymethyl celluloses with a low degree of substitution, hydroxypropyl celluloses with a low degree of substitution, calcium carboxymethyl celluloses, alginic acid, cross-linked carboxyymethyl celluloses and cross-linked polyvinyl pyrrolidones.

It is also known that the effect of disintegrating agents and the disintegration of tablets can be strongly influenced by excipients and/or active ingredients which are readily soluble in water, since disintegration of the tablet is impeded due to the decrease in volume during the dissolution of the attendant materials. Moreover, water-soluble substances exhibit the properties of binders to a certain extent, and capillaries in the tablet are closed by the rapid formation of a highly concentrated diffusion boundary layer. It was therefore proposed in published PCT application No. WO 87/01936 that water-soluble mannitol, optionally together with a disintegrating agent, be melted and subsequently ground for tablets having active ingredients which are difficultly soluble in water. The coarser particles which are thus produced, which have a preferred grain size between 0.1 and 0.6 mm, have a reduced solubility in water compared with untreated mannitol. Tablets having an active ingredient which is difficultly soluble in water which have been pressed with the melted, ground mannitol disintegrate very rapidly in water.

Rapidly dissolving tablets for difficultly soluble active ingredients are also known from published European Patent Application No. EP 124,027. These contain the active ingredient in a defined grain size distribution in combination with microcrystalline cellulose and starch.

According to German Auslegeschrift No. DE 1,617,343, in order to achieve a good disintegrating agent effect binders and excipients can be suspended together and subsequently spray-dried. The spray-dried mixture of excipients facilitates rapid disintegration of the tablets. Spray-dried tablets are also known from published European Patent Application No. EP 130,683 which contain N-acetyl-p-aminophenol as the active ingredient, as well as partially gelatinized starch, optionally in combination with microcrystalline celluloses as an additional disintegrating agent. However, at 3 to 5 minutes, the time of disintegration of these spray-dried tablets, which have a pharmaceutically acceptable hardness, must be classified as moderate.

It is known from U.S. Pat. No. 3,181,998 that the delay in the disintegration of pressed articles caused by binders can be counteracted if enzymes in their dry state are incorporated into the drug formulation. The enzymes are activated on contact with water or digestive juices and accelerate the disintegration of the tablets by cleavage of the starches, cellulose derivatives or gelatins used as binders.

Another factor which affects the rate of disintegration of tablets is the hardness of the tablet. High compaction forces during tabletting result in high tablet hardness, namely high binding forces inside the pressed article which make disintegration on contact with aqueous medium more difficult. Attempts are made in U.S. Pat. No. 5,254,355 to solve this problem by pressing dry mixtures to form tablets with very low hardness less than 35 N and subsequently increasing the hardness by at least 10 N by glazing the tablet surface. The result of this is that the binding forces remain low inside the tablets and good disintegration becomes possible.

In the effervescent tablets known from published German Patent Application No. DE 3,909,520, the rapid disintegration of the tablet is promoted by excipients which evolve $CO_2$ on contact with water.

Tramadol hydrochloride-(1 RS; 2 RS)-2-[(dimethylamino) methyl]-1-(3 -methoxyphenyl) cyclohexanol hydrochloride -is an analgesic which is effective for intense and moderately intense pain. However, the very high water solubility of this active ingredient has hitherto prevented the successful development of tablets which disintegrate rapidly in water. For example, if tramadol is mixed with an insoluble excipient such as calcium dihydrogen phosphate and a super-disintegrating agent such as Kollidon™ CL and granulated, the resulting tablets, which have a hardness of 80N, require 5 minutes for complete disintegration. Disintegration cannot even be accelerated by increasing the content of disintegrating agent. A disintegration rate of 5 minutes is unacceptable for a tablet which should disintegrate rapidly in water and release the active ingredient rapidly, however.

SUMMARY OF THE INVENTION

It is therefore the object of the present invention to provide a tablet containing tramadol or a pharmaceutically acceptable tramadol salt which disintegrates rapidly in water and releases the active ingredient rapidly, so that a suspension is available which contains the active ingredient and which can be drunk immediately.

It has been found that the requirements imposed on the form of medication to be developed are fulfilled by binder-free tablets which contain tramadol or a tramadol salt in combination with microcrystalline cellulose in defined weight ratios.

Accordingly, the present invention relates to binder-free tablets for oral administration, which contain microcrystalline cellulose and tramadol or a pharmaceutically acceptable tramadol salt in a weight ratio of at least 2:1.

DETAILED DESCRIPTION OF PREFERRED EMBODIMENTS

Binder-free tablets are preferred in which the weight ratio of microcrystalline cellulose to tramadol or a tramadol salt is at least 3:1 and in particular is at least 4:1.

The tablets according to the invention disintegrate very rapidly in water and release tramadol or tramadol salt very rapidly. Thus a drinkable suspension containing the active ingredient is produced immediately after the tablet according to the invention is brought into contact with water. The tablets according to the invention, before they are taken, make use of the positive properties of a solid form of medication such as exact dosage, good storage life, the possibility of using hygienic packaging and the omission of preservatives, and when they are taken, they make use of the positive properties of a liquid form of medication, for example ease of swallowing, and a rapid flow of the active ingredient into the bloodstream.

Tablets according to the invention are particularly preferred which contain starch, particularly in a weight ratio of starch to tramadol or tramadol salt of 1:1. In these tablets the effect of tablet hardness on the rate of disintegration is significantly reduced. When the hardness of tablets according to the invention which contain no starch (Example 1) is increased from 80N to 100N, the time of disintegration increases from 30 seconds to 120 seconds. In contrast, the time of disintegration of a tablet according to the invention which contains starch (Example 2) increases from 30 seconds to only 55 seconds when the hardness is increased from 80N to 100N. Moreover, tablets according to the invention which contain starch exhibit an accelerated release of active ingredient.

In tablets according to the invention, the weight ratio of microcrystalline cellulose to tramadol/tramadol salt to starch is at least 2:1:1. If the proportion by weight of microcrystalline cellulose in relation to tramadol/tramadol salt and starch is less than this, the disintegration rate of the tablets decreases considerably. Moreover, the replacement of microcrystalline cellulose by water-soluble lactose or water-insoluble calcium hydrogen phosphate results in a significant decrease in disintegration rate.

The tablets according to the invention contain 5 to 1000 mg, preferably 10 to 200 mg, of tramadol and/or a pharmaceutically acceptable tramadol salt, particularly tramadol hydrochloride, per tablet.

The tablets according to the invention may contain, as optional ingredients, 0.5 to 10 percent by weight of at least one disintegrating agent, for example cross-linked polyvinyl pyrrolidone (PVP-CL), cross-linked carboxymethyl cellulose and/or sodium carboxymethyl starch, and up to 20 percent by weight of flavor-enhancing substances, such as sweetening agents, e.g. sodium saccharine, sodium cyclamate and/or aspartame, as well as flavorings e.g. fruit and/or herb flavorings.

The tablets according to the invention are preferably produced by mixing the constituents and subsequently compacting the resulting mixture.

EXAMPLES

Tablet hardnesses were determined using a Heberlein hardness determination device (Model 2E/205).

Example 1

10.000 g tramadol hydrochloride
44.400 g microcrystalline cellulose
2.000 g sodium saccharin
1.000 g peppermint flavoring
2.000 g aniseed flavoring
400 g micro-dispersed (colloidal) silica, and
200 g magnesium stearate were mixed in a container mixer to produce 200,000 tablets. The mixture was then passed through a 0.6 mm screen and mixed again in a container mixer.. Subsequent tabletting was carried out on a Fette P 2000 tablet press. The resulting tablets, which had a diameter of 10 mm and an average height of 3.2 mm, had an average weight of 300 mg and a hardness between 60 and 80N.

Example 2

200.000 tablets were produced, under the conditions given in Example 1, from:

10.000 g tramadol hydrochloride
48.400 g microcrystalline cellulose
10.000 g maize starch
2.000 g sodium saccharin
1.000 g peppermint flavoring
2.000 g aniseed flavoring
400 g micro-dispersed silica, and
200 g magnesium stearate.

The resulting tablets, which had a diameter of 10 mm and an average height of 3.9 mm, had an average weight of 370 mg and a hardness between 60 and 80N.

Example 3

200,000 tablets were produced, under the conditions given in Example 1, from:

10.000 g tramadol hydrochloride
29.400 g microcrystalline cellulose
10.000 g maize starch
2.000 g sodium saccharin
1.000 g peppermint flavoring
2.000 g aniseed flavoring
400 g micro-dispersed silica, and
200 g magnesium stearate.

The resulting tablets, which had a diameter of 10 mm and an average height of 3.9 mm, had an average weight of 275 mg and a hardness between 60 and 80N.

Example 4

200,000 tablets were produced, under the conditions given in Example 1, from:

10.000 g tramadol hydrochloride
20.400 g microcrystalline cellulose
10.000 g maize starch
2.000 g sodium saccharin
1.000 g peppermint flavoring
2.000 g aniseed flavoring
400 g micro-dispersed silica, and
200 g magnesium stearate.

The resulting tablets, which had a diameter of 10 mm and an average height of 3.9 mm, had an average weight of 230 mg and a hardness between 60 and 80 N.

Example 5

200,000 tablets were produced, under the conditions given in Example 1, from:

10.000 g tramadol hydrochloride
20.140 g microcrystalline cellulose
10.000 g maize starch
2.000 g sodium saccharin
260 g cross-linked polyvinyl pyrrolidone
1.000 g peppermint flavoring
2.000 g aniseed flavoring
400 g micro-dispersed silica, and
200 g magnesium stearate.

The resulting tablets, which had a diameter of 10 mm and an average height of 3.9 mm, had an average weight of 230 mg and a hardness between 60 and 80N.

Example 6 (comparison)

200,000 tablets with the composition given in Example 2 were produced under the conditions given in Example 1, except that water-soluble lactose was used instead of microcrystalline cellulose.

Example 7 (comparison)

200,000 tablets with the composition given in Example 2 were produced under the conditions given in Example 1, except that insoluble calcium hydrogen phosphate was used instead of microcrystalline cellulose.
Determination of the disintegration time and lease time of tablets containing tramadol Release times were determined spectrophotometrically according to Ph. Eur./DAB in a blade agitator apparatus, in 600 ml of gastric juice with a pH of 1.2. The temperature the release medium was 37±0.5° C., and the stirring speed was 75 rpm. Disintegration times were determined using an Erweka disintegration tester (Z T6-1-D).

The results are summarized in the following Table:

| Tablets according to Example No. | Disintegration[1] after | Release[1] of tramadol in % after | | | | | |
|---|---|---|---|---|---|---|---|
| | | 1 min | 2 min | 3 min | 4 min | 5 min | 6 min |
| 1 | 25–30 sec | 2.5 | 65.8 | 94.1 | >99 | >99 | >99 |
| 2 | 25–30 sec | 3.7 | >99 | >99 | >99 | >99 | >99 |
| 3 | 50–60 sec | 2 | 78.9 | >99 | >99 | >99 | >99 |
| 4 | 100–110 sec | 0.9 | 47.4 | 75.2 | 87.4 | 92.0 | >99 |
| 5 | 110 sec | 1.2 | 62.0 | 97.8 | >99 | >99 | >99 |
| 6 (comparison) | >10 min | 0.1 | 10.2 | 25.2 | 38.2 | 50.2 | 89.5 |
| 7 (comparison) | 360 sec | 0.1 | 10.3 | 24.5 | 38.5 | 52.6 | 85.4 |

[1] sec denotes seconds; min denotes minutes

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A binder-free tablet containing an effective analgesic amount of tramadol or a tramadol salt for oral administration, said tablet comprising microcrystalline cellulose and tramadol or a pharmaceutically acceptable tramadol salt in a weight ratio of at least 2:1.

2. A tablet according to claim 1, wherein said tablet comprises microcrystalline cellulose and tramadol or a tramadol salt in a weight ratio of at least 3:1.

3. A tablet according to claim 1, wherein said tablet comprises microcrystalline cellulose and tramadol or a tramadol salt in a weight ratio of at least 4:1.

4. A tablet according to claim 1, wherein said tablet further comprises starch.

5. A tablet according to claim 4, wherein the weight ratio of starch to tramadol or tramadol salt is 1:1.

6. A tablet according claim 1, further comprising 0.5 to 10 percent by weight of at least one disintegrating agent.

* * * * *